United States Patent
Watanabe et al.

(10) Patent No.: US 6,500,971 B2
(45) Date of Patent: Dec. 31, 2002

(54) ESTER COMPOUNDS HAVING ALICYCLIC AND OXIRANE STRUCTURES AND METHOD FOR PREPARING THE SAME

(75) Inventors: Takeru Watanabe, Nakakubiki-gun (JP); Takeshi Kinsho, Nakakubiki-gun (JP); Koji Hasegawa, Nakakubiki-gun (JP); Tsunehiro Nishi, Nakakubiki-gun (JP); Mutsuo Nakashima, Nakakubiki-gun (JP); Seiichiro Tachibana, Nakakubiki-gun (JP); Jun Hatakeyama, Nakakubiki-gun (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 09/873,193

(22) Filed: Jun. 5, 2001

(65) Prior Publication Data
US 2002/0035279 A1 Mar. 21, 2002

(30) Foreign Application Priority Data
Jun. 6, 2000 (JP) ......................................... 2000-169357

(51) Int. Cl.[7] ...................... C07D 303/16; C07D 301/30
(52) U.S. Cl. ....................................... 549/549; 549/519
(58) Field of Search .................................. 549/519, 549

(56) References Cited

U.S. PATENT DOCUMENTS 4,351,748 A * 9/1982 Delay ..................... 252/522 R

* cited by examiner

Primary Examiner—Ba K. Trinh
(74) Attorney, Agent, or Firm—Millen, White, Zelano & Branigan, P.C.

(57) ABSTRACT

An ester compound of formula (1) is provided.

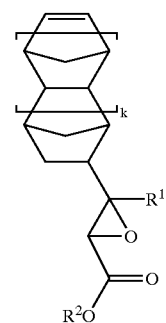

(1)

$R^1$ is H or methyl, $R^2$ is tertiary $C_{4-20}$ alkyl, and k=0 or 1. A resist composition comprising as the base resin a polymer resulting from the ester compound is sensitive to high-energy radiation, has excellent sensitivity, resolution, etching resistance and substrate adhesion, and is suited for micropatterning using electron beams or deep-UV.

5 Claims, No Drawings

ESTER COMPOUNDS HAVING ALICYCLIC AND OXIRANE STRUCTURES AND METHOD FOR PREPARING THE SAME

BACKGROUND OF THE INVENTION

1. Field of the Invention

The present invention relates to novel ester compounds having alicyclic and oxirane structures which form polymers useful as a base resin to formulate a chemical amplification type resist composition adapted for microfabrication, and a method for preparing the same.

2. Prior Art

While a number of recent efforts are being made to achieve a finer pattern rule in the drive for higher integration and operating speeds in LSI devices, deep-ultraviolet lithography is thought to hold particular promise as the next generation in microfabrication technology. In particular, photolithography using a KrF or ArF excimer laser as the light source is strongly desired to reach the practical level as the micropatterning technique capable of achieving a feature size of 0.3 µm or less.

The resist materials for use in photolithography using light of an excimer laser, especially ArF excimer laser having a wavelength of 193 nm, are, of course, required to have a high transmittance to light of that wavelength. In addition, they are required to have an etching resistance sufficient to allow for film thickness reduction, a high sensitivity sufficient to eliminate any extra burden on the expensive optical material, and especially, a high resolution sufficient to form a precise micropattern. To meet these requirements, it is crucial to develop a base resin having a high transparency, rigidity and reactivity. None of the currently available polymers satisfy all of these requirements. Practically acceptable resist materials are not yet available.

Known high transparency resins include copolymers of acrylic or methacrylic acid derivatives and polymers containing in the backbone alicyclic compounds derived from norbornene derivatives. All these resins are unsatisfactory. For example, copolymers of acrylic or methacrylic acid derivatives are relatively easy to increase reactivity in that highly reactive monomers can be introduced and acid labile units can be increased as desired, but difficult to increase rigidity because of their backbone structure. On the other hand, the polymers containing alicyclic compounds in the backbone have rigidity within the acceptable range, but are less reactive with acid than poly(meth)acrylate because of their backbone structure, and difficult to increase reactivity because of the low flexibility of polymerization. Additionally, since the backbone is highly hydrophobic, these polymers are less adherent to substrates. Therefore, some resist compositions which are formulated using these polymers as the base resin fail to withstand etching although they have satisfactory sensitivity and resolution. Some other resist compositions are highly resistant to etching, but have low sensitivity and low resolution below the practically acceptable level.

SUMMARY OF THE INVENTION

An object of the invention is to provide a novel ester compound having alicyclic and oxirane structures useful as a monomer to form a polymer for use in the formulation of a photoresist composition which exhibits improved adhesion and transparency when processed by photolithography using light with a wavelength of less than 300 nm, especially ArF excimer laser light as the light source. Another object is to provide a method for preparing the ester compound.

We have found that ester compounds of the general formula (1) can be prepared in high yields by a simple process to be described later; that a polymer obtained using the ester compound has high transparency at the exposure wavelength of an excimer laser; and that a resist composition using the polymer as a base resin is fully adherent.

In one aspect, the invention provides an ester compound of the following general formula (1).

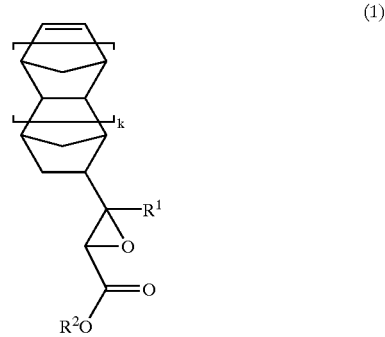

(1)

Herein $R^1$ is hydrogen or methyl, $R^2$ is a tertiary alkyl group of 4 to 20 carbon atoms, and k is 0 or 1.

Preferably the ester compound of formula (1) is represented by the following general formula (2) or (3).

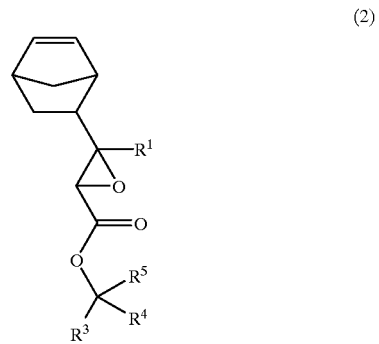

(2)

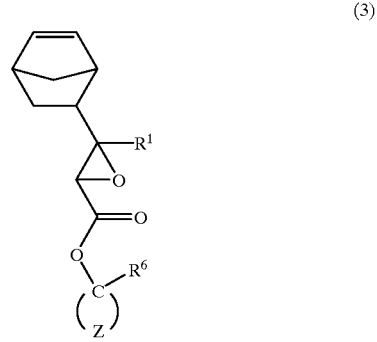

(3)

Herein $R^1$ is hydrogen or methyl, $R^3$, $R^4$, $R^5$, and $R^6$ are independently straight, branched or cyclic alkyl groups of 1 to 15 carbon atoms, and Z is a divalent hydrocarbon group of 4 to 15 carbon atoms which forms a ring with the carbon atom to which it is connected at both ends.

From a process aspect, the ester compound of the general formula (1) is prepared by effecting Darzen's reaction between a carbonyl compound of the following general formula (4) and a haloacetate compound of the following general formula (5) in the presence of a base according to the following reaction scheme.

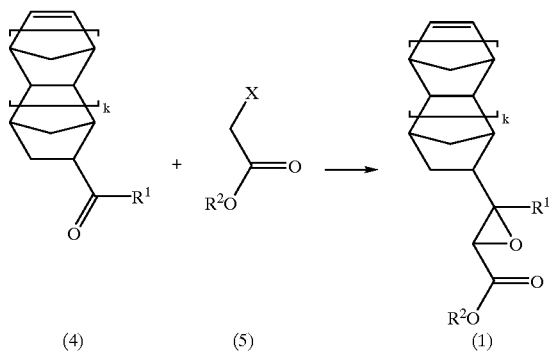

Herein $R^1$, $R^2$ and k are as defined above and X is a chlorine or bromine atom.

DESCRIPTION OF THE PREFERRED EMBODIMENT

The ester compounds of the invention are of the following general formula (1).

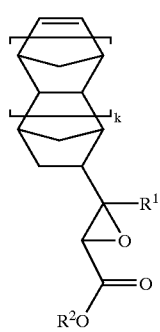

Herein $R^1$ is hydrogen or methyl, $R^2$ is a tertiary alkyl group of 4 to 20 carbon atoms, and k is 0 or 1.

As the partial structure $OR^2$, those of the following general formulas are preferred.

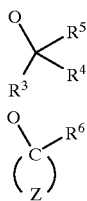

Herein $R^3$, $R^4$, $R^5$, and $R^6$ are independently straight, branched or cyclic alkyl groups of 1 to 15 carbon atoms. Z is a divalent hydrocarbon group of 4 to 20 carbon atoms such as a straight, branched or cyclic alkylene or alkenylene group, which forms a ring with the carbon atom to which it is connected at opposite ends.

Examples of the $C_{1-15}$ alkyl groups represented by $R^3$, $R^4$, $R^5$, and $R^6$ include methyl, ethyl, n-propyl, isopropyl, n-butyl, isobutyl, sec-butyl, tert-butyl, n-pentyl, n-hexyl, cyclopentyl, cyclohexyl, methylcyclopentyl, ethylcyclopentyl, methylcyclohexyl, ethylcyclohexyl, bicyclo[2.2.1]heptyl, bicyclo[2.2.2]octyl, bicyclo[3.3.1]-nonyl, bicyclo[4.4.0]decanyl, tricyclo[5.2.1.0$^{2,6}$]decanyl, tetracyclo[4.4.0.1$^{2,5}$.1$^{7,10}$]dodecanyl, and adamantyl. Examples of the rings that the divalent hydrocarbon group Z forms with the carbon atom include cyclopentane, cyclopentene, cyclohexane, cyclohexene, bicyclo[2.2.1]heptane, bicyclo[4.4.0]decane, tricyclo[5.2.1.0$^{2,6}$]decane, tetracyclo[4.4.0.1$^{2,5}$.1$^{7,10}$]dodecane, and adamantane.

Of the ester compounds of formula (1), preferred are those of the following general formula (2) or (3).

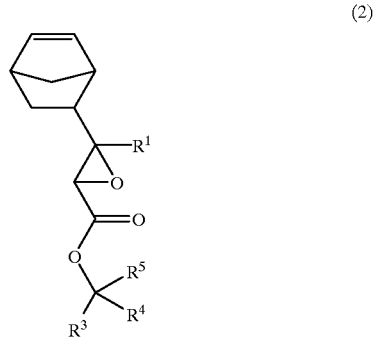

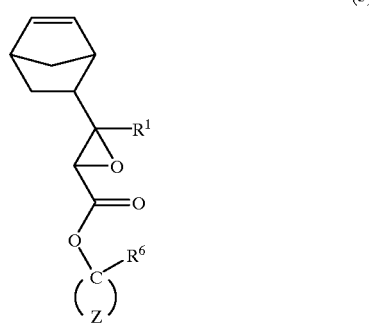

Herein $R^1$, $R^3$, $R^4$, $R^5$, $R^6$ and Z are as defined above.

Illustrative, non-limiting, examples of the ester compounds of the formula (1) and especially formula (2) or (3) include those of the following structures.

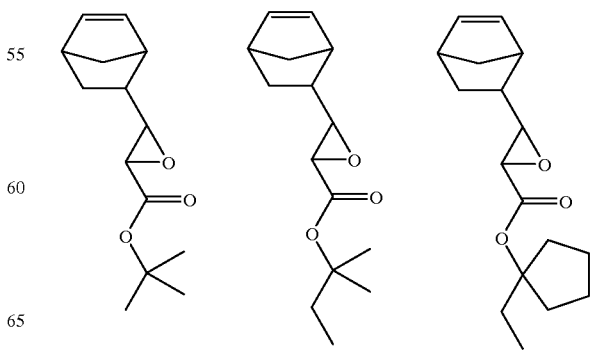

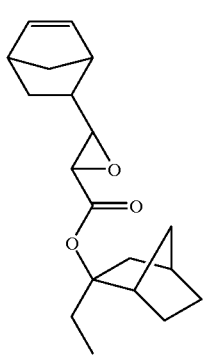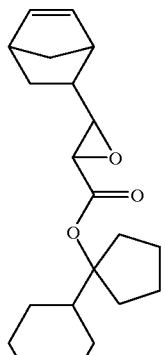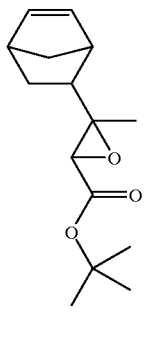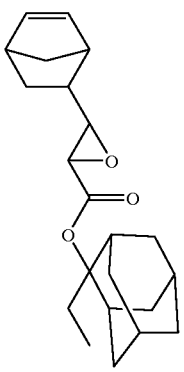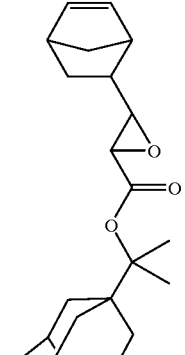

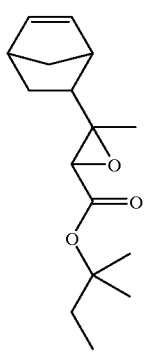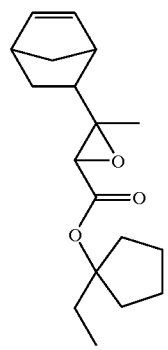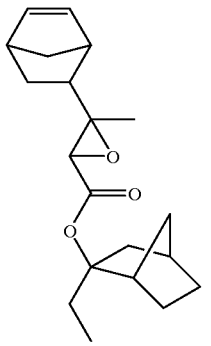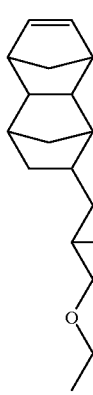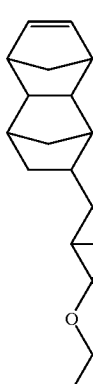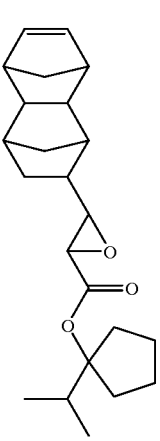

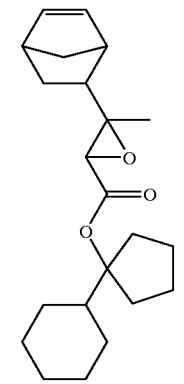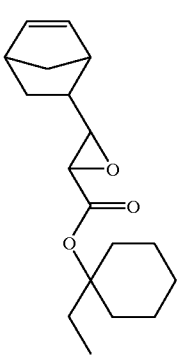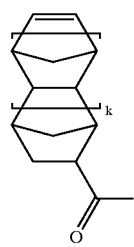

The ester compound of the invention can be synthesized, for example, by effecting Darzen's reaction, also known as Darzen's condensation, between a carbonyl compound of the following general formula (4) and a haloacetate compound of the following general formula (5) in the presence of a base according to the following reaction scheme.

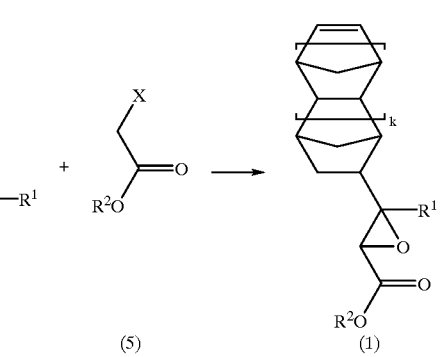

Herein $R^1$, $R^2$ and k are as defined above and X is a chlorine or bromine atom.

The bases used herein include metal amides such as sodium amide, potassium amide, lithium diisopropylamide, potassium diisopropylamide, lithium dicyclohexylamide, potassium dicyclohexylamide, lithium 2,2,6,6-tetramethylpiperidine, lithium bistrimethylsilylamide, sodium bistrimethylsilylamide, potassium bistrimethylsilylamide, lithium isopropylcyclohexylamide, and bromomagnesium diisopropylamide: alkoxides such as sodium methoxide, sodium ethoxide, lithium methoxide, lithium ethoxide, lithium tert-butoxide, and potassium tert-butoxide; inorganic hydroxides such as sodium hydroxide, lithium hydroxide, potassium hydroxide, barium hydroxide, and tetra-n-butylammonium hydroxide; inorganic carbonates such as sodium carbonate, sodium hydrogen carbonate, lithium carbonate and potassium carbonate; metal hydrides such as sodium hydride, lithium hydride, potassium hydride, and calcium hydride; and alkyl metal compounds such as trityl lithium, trityl sodium, trityl potassium, methyl lithium, phenyl lithium, sec-butyl lithium, tert-butyl lithium, and ethyl magnesium bromide, but are not limited thereto.

Upon reaction, the molar ratio of the compounds of formulas (4) and (5) may be selected as appropriate although it is preferred to use the compound of formula (5) in an amount of about 0.5 to 1.5 moles, especially about 0.8 to 1.2 moles per mole of the carbonyl compound of formula (4). It is also preferred to use the base in an amount of about 0.5 to 2.0 moles, especially about 0.8 to 1.5 moles per mole of the carbonyl compound of formula (4).

Useful solvents are ethers such as tetrahydrofuran, diethyl ether, di-n-butyl ether, and 1,4-dioxane, hydrocarbons such as n-hexane, n-heptane, benzene, toluene, xylene and cumene, alcohols such as methanol, ethanol, isopropyl alcohol and tert-butyl alcohol, amines such as liquid ammonia and methylamine, and aprotic polar solvents such as dimethyl sulfoxide and N,N-dimethylformamide. Depending on reaction conditions, a choice may be made among these solvents alone and mixtures thereof. There may also be subordinately used any of compounds having ligands such as N,N,N',N'-tetramethylethylenediamine (TMEDA), hexamethylphosphorous triamide (HMPA), N,N'-dimethylpropyleneurea (DMPU) and 1,3-dimethyl-2-imidazolidinone (DMI).

Where inorganic hydroxides or inorganic carbonates are used as the base, reaction may be effected in a concomitant system of the aforementioned organic solvent and water, that is, two-layer system. In this case, a phase transfer catalyst such as a quaternary ammonium salt or quaternary phosphonium salt may be added for promoting or accelerating the reaction.

The reaction temperature depends on other reaction conditions. When a strong base is employed in an organic solvent, the reaction favors cooling at a temperature between −78° C. and 10° C. In the case of two-layer system reaction, the temperature usually ranges from ice cooling to room temperature, and even heating up to about 60° C. is acceptable.

From the reaction mixture, the desired compound is obtained by a conventional aqueous work-up step. If necessary, the desired compound is purified by any conventional technique such as distillation, chromatography or recrystallization.

A polymer is prepared using the inventive ester compound as a monomer. One common procedure is by mixing the monomer with a solvent, adding a catalyst or polymerization initiator, and effecting polymerization reaction while heating or cooling the system if necessary. This polymerization reaction can be effected in a conventional way.

A resist composition is formulated using as a base resin the polymer resulting from polymerization of the ester compound. Usually, the resist composition is formulated by adding an organic solvent and a photoacid generator to the polymer and if necessary, further adding a crosslinker, a basic compound, a dissolution inhibitor and other additives. Preparation of the resist composition can be effected in a conventional way.

The resist composition formulated using the polymer resulting from polymerization of the inventive ester compound lends itself to micropatterning with electron beams or deep-UV rays since it is sensitive to high-energy radiation and has excellent sensitivity, resolution, and etching resistance. Especially because of the minimized absorption at the exposure wavelength of an ArF or KrF excimer laser and firm adhesion to the substrate, a finely defined pattern having sidewalls perpendicular to the substrate can easily be formed. The resist composition is thus suitable as micropatterning material for VLSI fabrication.

EXAMPLE

Synthesis Examples and Reference Examples are given below for further illustrating the invention. It is not construed that the invention be limited to these examples.

Synthesis Examples are first described. Ester compounds within the scope of the invention were synthesized by the following method.

Synthesis Example 1

Synthesis of tert-butyl 2,3-epoxy-3-(5-norbornen-2-yl)-propionate (Monomer 1)

In a nitrogen atmosphere, a solution of 112 g of potassium tert-butoxide in 400 g of dry tetrahydrofuran was added dropwise over 2 hours to a mixture of 122 g of 5-norbornene-2-carbaldehyde, 151 g of tert-butyl chloroacetate, and 500 g of dry tetrahydrofuran at 0–5° C. After one hour of stirring, 400 g of water was added to stop the reaction. The organic layer obtained by hexane extraction was washed with water, dried over anhydrous sodium sulfate, filtered, and concentrated in vacuo. Purification by vacuum distillation yielded 224 g (yield 95%) of tert-butyl 2,3-epoxy-3-(5-norbornen-2-yl)propionate as a fraction having a boiling point of 92–94° C./53 Pa.

IR (thin film): ν=3059, 2976, 2939, 2870, 1747, 1724, 1439, 1392, 1369, 1336, 1309, 1250, 1221, 1157, 1122 cm$^{-1}$ $^{1}$H-NMR (300 MHz in CDCl$_3$): δ=0.70–2.20 {(14H, m) including (9H, s)}, 2.55–3.50 (4H, m), 5.90–6.25 (2H, m)

Synthesis Example 2

Synthesis of 1-ethylcyclopentyl 2,3-epoxy-3-(5-norbornen-2-yl)propionate (Monomer 2)

The procedure of Synthesis Example 1 was repeated except that 1-ethylcyclopentyl chloroacetate was used instead of tert-butyl chloroacetate, and purification conducted by silica gel chromatography instead of vacuum distillation. There was synthesized 1-ethylcyclopentyl 2,3-epoxy-3-(5-norbornen-2-yl)propionate (yield 97%). IR (thin film): ν=3059, 2970, 2872, 1745, 1722, 1446, 1439, 1336, 1282, 1250, 1211, 1173 cm$^{-1}$ $^{1}$H-NMR (270 MHz in CDCl$_3$): δ=0.60–2.25 {(18H, m) including (3H, t, J=7.3 Hz) and (2H, q, J=7.3 Hz)}, 2.55–3.50 (4H, m), 5.90–6.25 (2H, m)

Synthesis Example 3

Synthesis of 2-ethyl-2-exo-norbornyl 2,3-epoxy-3-(5-norbornen-2-yl)propionate (Monomer 3)

The procedure of Synthesis Example 2 was repeated except that 2-ethyl-2-exo-norbornyl chloroacetate was used instead of 1-ethylcyclopentyl chloroacetate. There was synthesized 2-ethyl-2-exo-norbornyl 2,3-epoxy-3-(5-norbornen-2-yl)propionate (yield 97%).

IR (thin film): ν=3059, 2968, 2872, 1745, 1720, 1458, 1441, 1383, 1333, 1313, 1296, 1252, 1201, 1173, 1132, 1115 cm$^{-1}$ $^{1}$H-NMR (300 MHz in CDCl$_3$): δ=0.70–2.40 (19H, m), 2.50–3.50 (5H, m), 5.90–6.25 (2H, m)

The structural formulas of Monomers 1 to 3 are shown below.

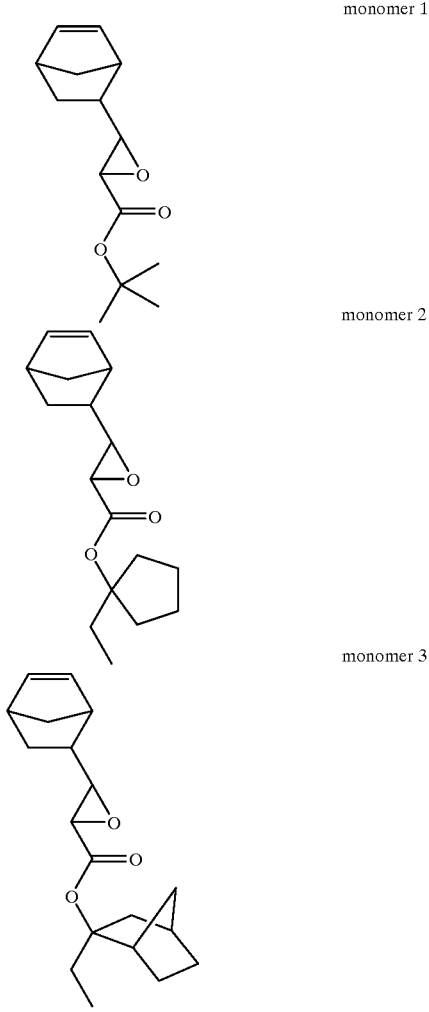

monomer 1 monomer 2 monomer 3

Reference Example

Polymers were synthesized using the ester compounds obtained in the above Synthesis Examples. Using the polymers as a base resin, resist compositions were formulated, which were examined for substrate adhesion.

Polymerization reaction of Monomer 1 and maleic anhydride was effected using the initiator V65 (Wako Junyaku K. K.), yielding an alternating copolymer of tert-butyl 2,3-epoxy-3-(5-norbornen-2-yl)propionate/maleic anhydride.

A resist composition was prepared by blending 80 parts by weight of the above copolymer as a base resin, 1.0 part by weight of triphenylsulfonium trifluoromethanesulfonate as a photoacid generator, 480 parts by weight of propylene glycol monomethyl ether acetate as a solvent, and 0.08 part by weight of tributylamine. The composition was spin coated on a silicon wafer having hexamethyldisilazane sprayed thereon at 90° C. for 40 seconds and heat treated at 110° C. for 90 seconds, forming a resist film of 500 nm thick. The resist film was exposed to KrF excimer laser light, heat treated at 110° C. for 90 seconds, and developed by immersing in a 2.35% aqueous tetramethylammonium hydroxide solution for 60 seconds, thereby forming a 1:1 line-and-space pattern. The wafer as developed was observed under SEM, finding that the pattern down to 0.26 μm size was left unstripped.

Comparative Reference Example

For comparison purposes, a resist composition was prepared as above, using an alternating copolymer of tert-butyl 5-norbornene-2-carboxylate/maleic anhydride. It was similarly processed, and examined for substrate adhesion. No patterns with a size of 0.50 μm or less were left.

It was confirmed that polymers resulting from the inventive ester compounds have significantly improved substrate adhesion as compared with prior art polymers.

Japanese Patent Application No. 2000-169357 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. An ester compound of the following general formula (1):

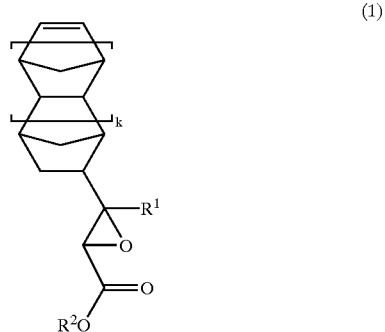

(1)

wherein $R^1$ is hydrogen or methyl, $R^2$ is a tertiary alkyl group of 4 to 20 carbon atoms, and k is 0 or 1.

2. The ester compound of claim 1 represented by the following general formula (2) or (3):

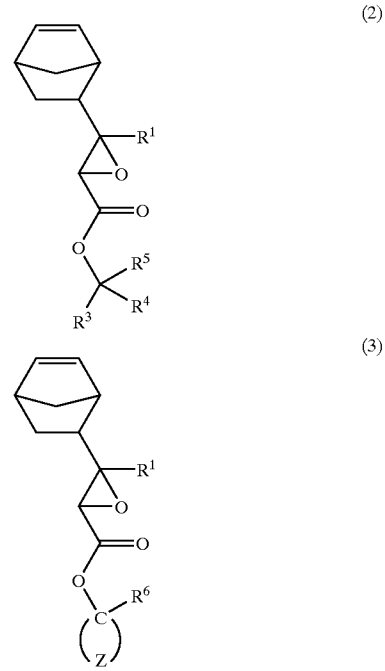

(2)

(3)

wherein $R^1$ is hydrogen or methyl, $R^3$, $R^4$, $R^5$, and $R^6$ are independently straight, branched or cyclic alkyl groups of 1 to 15 carbon atoms, and Z is a divalent hydrocarbon group of 4 to 15 carbon atoms which forms a ring with the carbon atom to which it is connected at opposite ends.

3. A method for preparing the ester compound of the general formula (1) as set forth in claim 1, comprising effecting Darzen's reaction between a carbonyl compound of the following general formula (4) and a haloacetate compound of the following general formula (5) in the presence of a base:

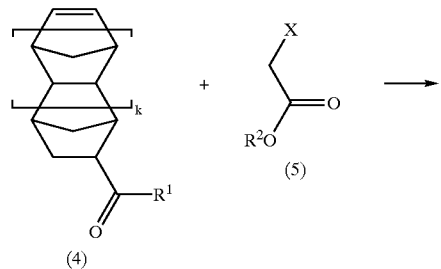

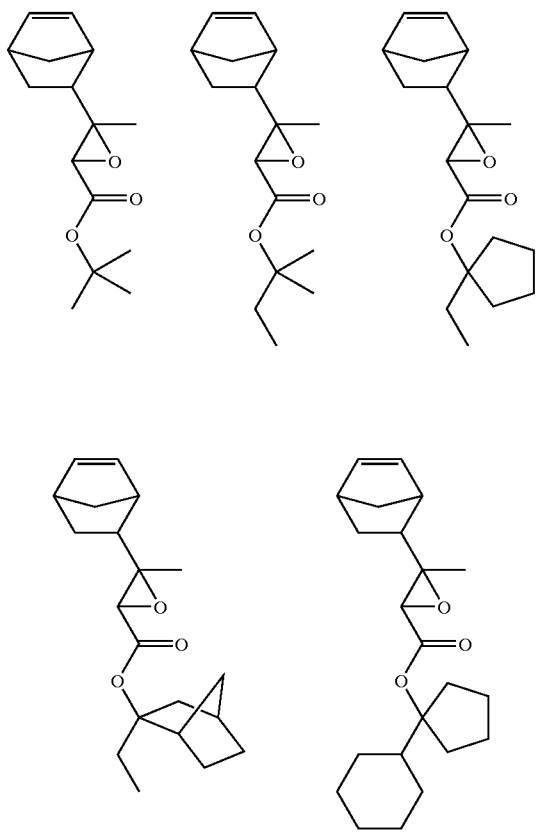

wherein $R^1$, $R^2$ and k are as defined above and X is a chlorine or bromine atom.

4. The ester compound of claim 1, which compound is of one of the following structures:

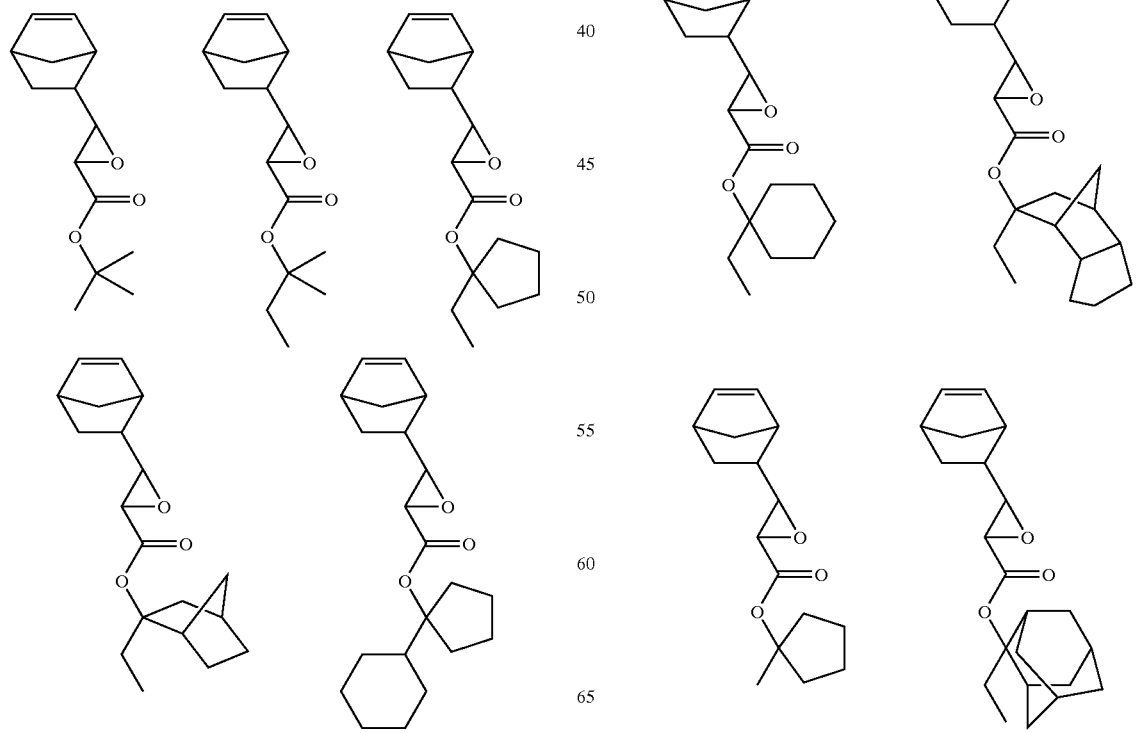

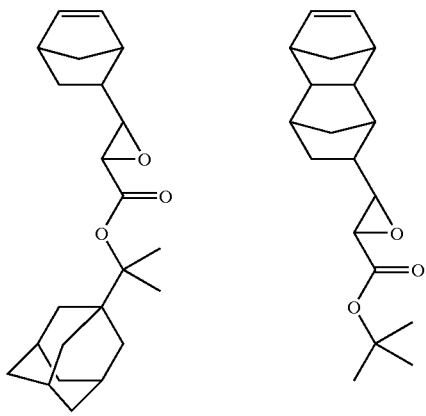
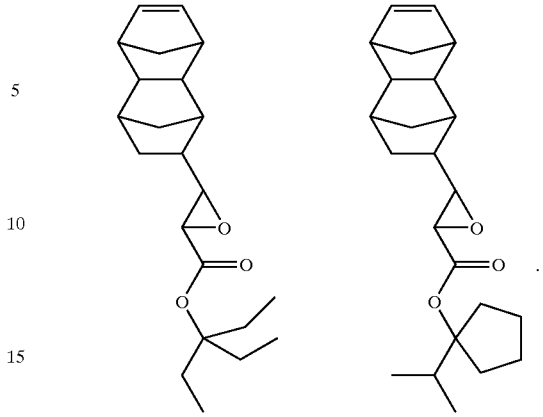
5. The ester compound of claim 1, wherein $R^2$ is tert-butyl, 1-ethylcyclopentyl, 2-ethyl-2-exo-norbornyl.
* * * * *